US006528247B1

(12) United States Patent
Noteborn

(10) Patent No.: US 6,528,247 B1
(45) Date of Patent: Mar. 4, 2003

(54) DETERMINING THE TRANSFORMING CAPABILITY OF AGENTS

(75) Inventor: Mathieu H. M. Noteborn, Leiderdorp (NL)

(73) Assignee: Leadd B.V., Leiden (NL)

( * ) Notice: Subject to any disclaimer, the term of this patent is extended or adjusted under 35 U.S.C. 154(b) by 0 days.

(21) Appl. No.: 09/485,551

(22) PCT Filed: Aug. 11, 1998

(86) PCT No.: PCT/NL98/00457

§ 371 (c)(1),
(2), (4) Date: May 5, 2000

(87) PCT Pub. No.: WO99/08108

PCT Pub. Date: Feb. 18, 1999

(30) Foreign Application Priority Data

Aug. 12, 1997 (EP) .............................................. 97202501

(51) Int. Cl.[7] .......................... C12Q 1/00; C12P 21/06; G01N 33/48
(52) U.S. Cl. .............................. 435/4; 435/69.1; 436/64
(58) Field of Search .............................. 435/320.1, 325, 435/348, 4, 69.1; 514/44; 424/204.1; 436/64

(56) References Cited

U.S. PATENT DOCUMENTS 5,491,073 A    2/1996    Noteborn et al. .......... 435/69.1

FOREIGN PATENT DOCUMENTS

| WO | WO 96/41191 | 12/1996 |
| WO | WO 98/00213 | 1/1998 |
| WO | WO 98/46760 | 10/1998 |

OTHER PUBLICATIONS

Abrahams, et al., *Cancer Research* (1992), 52:53–7.
Abrahams, et al., *Cancer Research* (1996), 56:2621–5.
Abrahams, et al., *Molecular Cellular Biology* (1984), 4:2341–6.
Bellamy, et al., *Seminars on Cancer Biology* (1995), 6:3–12.
Brinster, et al., *Science* (1981), 211:396–8.
Daneb–van Oorschot, et al., *Apoptosis* (1997).
Danen–van Oorschot, et al., *Proceedings National Academy Sciences, USA* (1997), 94:5843–7.
De Ronde, et al., *Virology* (1989), 171:260–3.
Dinsart, et al., *Molecular Cellular Biology* (1984), 4:324.
Drezen, et al., *J. of Immunology* (1992), 149:429–37.
Duke, et al., *Scientific American* (Dec. 1996), 48–55.
Earnshaw, *Current Opinion in Cell Biology* 7:337–43, 1995.
Fischer, et al., *Molecular and Cellular Biology* (1996), 16:5365–74.
Graham, et al., *Virology* (1973), 52:456–7.
Gruis, et al., *Nature Genetics* (1995), 10:351–3.
Hockenberry, *J. of Cell Science* (1994), Supp. 18:51–5.
Jacks, *Current Biology* (1994), 4:1–7.
Jacks, *J. of Cancer Res. And Clinical Oncology* (1996), 122:19–27.
Kerr, *Cancer* (1994), 73:2013–26.
Klein, et al., *Experimental Cellular Res.* (1990), 191:256–62.
Levine, *Cell* (1997), 88:323–31.
Lowe, et al., *Proceedings of the National Academy of Sciences, USA* (1994), 91:2026–30.
Maniatis, et al., *Molecular Cloning: A Laboratory Manual.* (1982), CSHL Press, NY.
McBurney, et al., *Developments in Biology* (1982), 89:503–8.
McDonell, et al., *Seminars in Cancer Biology* (1995), 6:53–60.
Mellor, et al., *Nature* (1982), 298:529–34.
Menke, et al., *Cancer Res.* (1997), 57:1353–63.
Morello, et al., *EMBO Journal* (1986), 5:1877–83.
Noteborn, et al., *Gene* (1992), 118:267–71.
Noteborn, et al., *J. of Virology* (1991), 65:3131–9.
Noteborn, et al., *J. of Virology* (1994), 68:346–51.
Noteborn, et al., *Gene*(1992), 118: 267–71.
Noteborn, et al., *J. Controlled Release* (1996), 41(1):10.
Paulovich, et al., *Cell* (1997), 88:315–21.
Philips, B., and Rundell, K., *J. of Virology* (1988), 62:768–75.
Pines, *Trends in Genetics* (1995), 11:326–7.
Ponec, et al., *J, Investmental Dermatology* (1981), 76:211–4.
Reinwald, *Cell* (1975), 6:331–43.
Sachs, L. and Lotem, J., *Blood* (1993), 52:15–21.
Schrier, et al., *Nature* (1983), 305:771–5.
Smiths, et al., *Virology* (1992), 190:40–4.
Southern, *J. of Molecular Biology* (1975), 98:503–17.
Srivastava, et al., *Nature* (1990), 348:747–9.
Steller, *Science* (1995), 267:1445–9.
Telford, et al., *Cytometry* (1992), 13:137–43.
Teodoro and Branton, *J. of Virology* (1997), 71:1739–46.
Thompson, *Science* (1995), 267:1456–62.
Van den Heuvel, et al., *EMBO Journal* (1990), 9:2621–9.
Van Laar, et al., *Oncogene* (1994), 9:981–3.
White, *Genes and Development* (1996), 10:1–15.
Wyllie, *Current Opinion in Genetics and Development* (1995), 5:97–104.
Wyllie, et al., *International Review of Cytology* (1980), 68:251–306.
Zhuang, et al., *Leukemia* (1995), 9(1):118–120.
Zhuang, et al., *Cancer Res.* (1995), 55:486–9.

*Primary Examiner*—Anthony C. Caputa
*Assistant Examiner*—Gary B. Nickol
(74) *Attorney, Agent, or Firm*—TraskBritt

(57) ABSTRACT

The invention related to activation of apoptin-induced apoptosis by different cell-transforming agents in normal and or cancer-prone cells. Apoptin, also called VP3, is a viral protein derived from the Chicken anemia virus. Also the invention related to preventive anti-tumor therapies of normal and/or cancer-prone cells. Treatment of normal and/or cancer prone cells with tumor-inducing agents will activate apoptin-induced apoptosis, resulting in the elimination of potential tumor cells. Also the invention relates to diagnosis of cancer agents. Agents with tumor activity can be examined by expressing them in normal cells and analyzing their capability of enabling apoptin-induced apoptosis.

10 Claims, 10 Drawing Sheets

Apoptin-induced apoptosis in normal rodent embryo fibroblasts versus transformed rodent cell lines Effect of SV40 LT+st, LT or st antigen on apoptin-induced apoptosis in VH10 and FSK-1

Location of apoptin in VH10 and FSK-1 expressing only apoptin or together with SV40 LT+st, LT or st antigen Effect of SV40 LT+st or LT antigen on apoptin-induced apoptosis in MEF(P53+/+) and MEF(p53-/-)

Location of apoptin in MEF(p53+/+) or MEF(p53-/-) expressing only apoptin or together with SV40 LT+st or LT antigen Effect of SV40 LT+st or LT antigen on apoptin-induced apoptosis in normal diploid human fibroblasts derived from cancer-prone individuals Effect of UV-irradiation on apoptin-induced apoptosis in normal diploid fibroblasts derived from healthy versus cancer-prone individuals

Overview VP3 transgenic mice

SEQUENCE LISTING

<160> NUMBER OF SEQ ID NOS: 3

<210> SEQ ID NO 1
<211> LENGTH: 8
<212> TYPE: PRT
<213> ORGANISM: Simian virus 40

<400> SEQUENCE: 1

Pro Pro Leu Leu Leu Arg Leu Val
1               5

<210> SEQ ID NO 2
<211> LENGTH: 25
<212> TYPE: DNA
<213> ORGANISM: Artificial Sequence
<220> FEATURE:
<223> OTHER INFORMATION: primer p1

<400> SEQUENCE: 2
ctctccaaca acatactcca cccgg                                           25

<210> SEQ ID NO 3
<211> LENGTH: 25
<212> TYPE: DNA
<213> ORGANISM: Artificial Sequence
<220> FEATURE:
<223> OTHER INFORMATION: primer p2

<400> SEQUENCE: 3
cttatacgcc tttttgcggt tcggg                                           25

DETERMINING THE TRANSFORMING CAPABILITY OF AGENTS

This application is a national stage filing under 35 U.S.C. §371 of PCT application PCT/NL98/000457 filed Aug. 11, 1998.

The present invention relates to the field of cancer diagnosis and treatment, as well as to the field of determining the transforming capability of suspected tumorigenic or tumor promoting agents (the two terms will be used interchangeably herein). The common denominator of the present invention is that all of the above fields are fields in which apoptin or derivatives and/or fragments thereof (hereinafter all referred to as apoptin or apoptin-like activity) can be applied according to the invention. Apoptin is a protein orginally found in Chicken Anemia Virus (Noteborn et al., 1991) and was originally called VP3. The apoptotic activity of this protein was discovered by the group of the present inventors (Noteborn et al., 1994). As stared above the present invention makes use of the apoptosis inducing effect of apoptin.

Apoptosis is an active and programmed physiological process for eliminating superfluous, excessively damaged or malignant celles (Earnshaw, 1995, Duke et al., 1996). Apoptosis is characterized by shrinkage of cells, segmentation of the nucleus and fragmentation of the cytoplasm, condensation and cleavage of DNA into domain-sized fragments, in most cases followed by internucleosomal degradation. The apoptotic cells become fragmented into membrane-enclosed apoptotic bodies. Finally, neighbouring cells and/or macrophages will rapidly phagocytose these dying cells (Wyllie et al., 1980, White, 1996). Cells grown under tissue-culture conditions and cells from tissues can be analysed for signs of apoptosis with agents staining chromosomal DNA, as e.g. DAPI or propidium iodide, which stains normal DNA (chromatic) strongly and regularly, but apoptotic chromatin weakly and/or irregularly (Noteborn et al., 1994, Telford et al., 1992).

The apoptotic process can be initiated by a variety of regulatory stimuli (Wyllie, 1995, White 1996, Levine, 1997). Changes in cell survival rate play an important role in human pathogenesis, e.g. in cancer development, which is caused by enhanced proliferation and/or by decreased cell death (Kerr et al., 1994, Paulovich, 1997). A variety of chemotherapeutic agents and radiation have been demonstrated to induce apoptosis in tumor cells which, in many instances is mediated via the tumor supressor protein p53 (Thompson, 1995, Bellamy et al., 1995, Steller, 1995, McDonell et al., 1995). Many tumors, however, acquire a mutation in p53 during their development, often correlating with poor response to cancer therapy. Transforming proteins of DNA tumor viruses inactivate p53 indirectly or by directly binding to it (Teodoro, 1997). An example of such an agent is the large T-antigen of the DNA tumor virus SV40. In certain hemopoietic tumors, a high expression level of the Bcl-2-oncogene is associated with a strong resistance to various apoptosis-inducing chemotherapeutic agents (Hockenberry 1994, Sachs and Lotem, 1997). For such cancers, that are resistant to many cytotoxic agents, alternative anti-tumor therapies are under development based on induction of apoptosis (Thompson, 1995 and Paulovch et al., 1997).

Apoptin is a small protein derived from the chicken anemia virus (CAV; Noteborn and De Boer, 1995, Noteborn et al., 1991, Noteborn et al., 1994), which can induce apoptosis in human malignant and transformed cell lines, but not in untransformed diploid human cells. In vitro, apoptin fails to induce programmed cell death in normal lymphoid, dermal fibroblastic, epidermal, endothelial and smooth-muscle cells. However, when normal cells are transformed e.g. by the transforming genes of SV40, they become susceptible to apoptosis by apoptin. (Danen-van Ooschot, 1997 and Noteborn, 1996). Long-term expression of apoptin in normal human fibroblasts revealed that apoptin has no toxic or transforming activity in these cells. In normal cells, apoptin was found to be localized predominantly in the cytoplasm, whereas in transformed or malignant cells, it was located in the nucleus, suggesting that the localization of apoptin is related to its death-inducing activity (Danen-van Oorschot et al. 1997).

Furthermore, we have established that apoptin can induce apoptosis in the absence of functional p53 (Zhuang et al., 1995a), and cannot be inhibited by Bcl-2, Bcr-abl (Zhuang et al., 1995), the Bcl-2-associating protein BAG-1 and the caspase-inhibitor cow-pox protein CrmA (Danen-Van Oorschot, 1997, Noteborn, 1996). Finally, it appears that cells that are only immortalized and thus minimally transformed, can also be killed by apoptin. Therefore, apoptin is an extremely potent anti-tumor agent, also for tumors that are not or less susceptible to (chemo)therapeutic agents due to the lack of functional p53, (over)-expression of Bcl-2 or other apoptosis-inhibiting genes. The fact that apoptin does not induce apoptosis in normal human cells, suggests that a toxic effect of apoptin treatment in vivo will be very low. In addition, it appears, that even premalignant, minimally transformed cells, may be sensitive to the death-inducing effect of apoptin. Knowing that apoptin is quite safe in normal cells, but that as soon as a cell becomes transformed and/or immortalized (the terms may be used interchangeably herein) the present inventors designed some uses based on this finding. Thus the invention provides a method for determining the transforming capability of a possible transforming agent, comprising providing a non-transformed cell with inducible apoptin-like apoptotic activity, exposing said cell to said transforming agent and determining the localization of said apoptotic activity within said cell or determining the induction of apoptosis in said cell. It is to be understood that in the above apoptotic activity also refers to the entity having said activity. It is preferred to provide said cell with said apoptotic activity by transducing said cell with a recombinant nucleic acid molecule encoding said activity. Apoptin-like activity is herein defined as any (preferably proteinaceous) substance having similar activity as VP3 or apoptin of chicken anemia virus. Specifically included in said definition are allelic variants, derivatives and/or fragments of apoptin, wherein derivatives are defined as having amino acid replacements which do not result in the loss of all apoptotic activity. It is to be understood that similar activity means that the kind of activity is the same although the amount may differ. The methods according to the invention are especially suitable in applications whereby said possible transforming agent is a proteinaceous substance. This allows for said proteinaceous substance to be co-expressed in said non-transformed cell with said apoptotic activity. The exemplified proteinaceous substance is the large T-antigen of SV40 or a functional equivalent thereof. The invention also provides modifications on the Apoptin gene resulting in changes on the apoptin protein enabling apoptin to enter the nucleus in non-transformed and transformed/tumorigenic cells, resulting in the induction of apoptosis. The apoptin protein is enlarged with a nuclear localization signal of SV40. Specifically included in said definition of apoptin are allelic variants, derivatives and/or fragments of apoptin, wherein derivatives are defined as having amino acid replacements which do not result in the loss of all apoptotic activity. This allows for the apoptin protein to be expressed in non-transformed cells with said apoptotic activity. Apoptin fragments with said apoptotic activity but not able to enter the nucleus of non-transformed or transformed cells by its own sequences, are able to enter the nucleus by means of the modifications and induce apoptosis.

The invention further provides a method for determining the predisposition of a cell to become a tumor cell, by providing said cell with inducible apoptin-like apoptotic activity and subjecting said cell to relatively mild tumorigenic activity and determining apoptosis in said cell and/or determining the localization of said apoptotic activity in said cell. In this case the suspected transforming agent as discussed hereinbefore is already present in said cell as a mutation leading to oncogenic or tumorigenic activity. In that case the fact that apoptin only induces apoptosis in cells which have already been transformed leads to the possibility to check whether cells have a mutation which will lead to immortalization or transformation upon mild exposure to transforming activity, such as UV-irradiation and X-ray treatment. In this manner the likelihood of a set of cells to lead to cancer can be determined. This of course leads to applications in the field of diagnosis of the chances of people having a hereditary risk of getting cancer and giving preventive treatment, which is another object of the present invention. This kind of diagnosis can also be applied in advising people of the likelihood of their children to be predisposed for cancer.

Thus the invention also provides a method for determining the predisposition of a subject for hereditary types of cancer, comprising subjecting a sample of a relevant subset of cells of such a subject to a method as disclosed herein. And the invention further provides a method for determining a gene mutation having oncogenic and/or transforming activity in a cell comprising subjecting said cell to a method according to the invention. As stated hereinbefore it is another object of the present invention to provide means for the prophylactic treatment of subsets of cells in a person, which subset of cells is cancer-prone. These means include a nucleic acid encoding apoptin-like activity, preferably provided in the form of a gene delivery vehicle. Gene delivery vehicles can be of viral origin or other. Many vehicles have been disclosed in the art and are known to the skilled person. They include but are not limited to adenoviral vectors, preferably in the form of adenoviral particles; retroviral vectors, preferably as recombinant retroviruses; the same kind of vectors but derived from other viruses; liposomes or other carrier molecules, etc. The invention also provides a diagnostic test kit for carrying out a method according to the invention in determining the tumorigenic capability of an agent, comprising a non-transformed cell transduced with a nucleic acid encoding apoptin or a functional derivative or fragment thereof and optionally all other material necessary to carry out the test and detecting the result. The invention further provides a diagnostic test kit for carrying out a method according to the invention for determining the cancer-proneness of cells, comprising a nucleic acid encoding apoptin or a functional derivative or fragment thereof capable of transducing a eukaryotic cell and capable of being expressed in such a cell and optionally all other material necessary to carry out the test and detecting the result. Preferably a means for subjecting a cell to a mid tumorigenic activity, such as UV-irradiation and X-ray treatment is also provided. The invention also provides a method for studying the induction of Apoptin-induced apoptosis by transforming agents such as chemicals, viruses, UV- and X-irradiation in a transgenic mouse model, which results in inhibition of tumor formation. The transgenic-apoptin mice can be used for analysing the anti-tumor effect of Apoptin in transgenic chimeras carrying hereditary types of cancer and able to express Apoptin. Furthermore, the effect of the expression of apoptin in an in-vivo model can be studied by means of the described transgenic-apoptin mice.

DETAILED DESCRIPTION OF THE INVENTION

We have previously shown that the viral protein apoptin induces apoptosis in cultured transformed cells of both human and rodent origin, but not in normal human cells. We have now observed that apoptin fails to induce apoptosis in cultured murine (or rat) embryonic fibroblasts. (the cultures were derived from 16–18 days old mouse (rat) embryos.) This shows that apoptin may also be expressed in the intact embryo without causing toxicity, at least embryos of a not too early stage of embryonic development.

We have now been able to produce transgenic-apoptin mice, which are viable. We provide evidence that constitutive expression of apoptin in a transgenic mouse does not result in lethal or other life-threatening/life-limiting effects. We have also observed that co-transfection of cultured normal human fibroblasts with the apoptin gene and the SV40 transforming genes will activate the apoptotic process, which is accompanied by translocation of the apoptin protein from the cytoplasm, where it accumulates initially, to the nucleus.

The described invention provides the basis for amino-acid additions to the apoptin protein or its fragments enabling those to enter and/or accumulate in the cellular nucleus, resulting in the induction of apoptosis.

The invention provides the basis for a diagnostic test for detection of potentially transforming genes. Normal diploid mammalian cells, such as human and/or rodent cells are used for such a test. To that end, the normal diploid cells are co-transfected with a plasmid containing the gene(s) to be studied and the plasmid encoding apoptin, or transfected with the gene(s) to be studied and infected with a viral vector expressing apoptin. Induction of apoptin-induced apoptosis and/or presence of apoptin in the nucleus show that the examined gene harbors transforming/tumorigenic potential.

Furthermore, we have discovered that diploid human cells isolated from individuals who carry a germ line mutation in a tumor-suppressor gene, and as a result are predisposed to develop a certain spectrum of tumors (herein also referred to as cancer-prone), are resistant to the apoptosis-inducing effect of apoptin, just as diploid cells from healthy individuals, however, become sensitive if the cell cultures are irradiated with ultraviolet light.

This allowed us to develop a diagnostic assay for predicting cancer-proneness. In families with a hereditary predisposition to cancer due to a germ-line mutation in a tumor suppressor gene, it is often not possible, without an extensive analysis of chromosomal DNA, to predict whether a family member is afflicted and carries the disease gene. Our results show that this is in a simple way, by making use of the apoptin gene. To that end, diploid skin fibroblasts or lymphocytes are isolated from the individual to be tested, and the cultured cells are transfected with the apoptin gene, followed by irradiation with UV-light (266 nm). If the transfected cells become apoptotic after UV irradiation but fail to enter apoptosis without UV exposure, then this is a (strong) indication that the individual is cancer-prone. Not all types of cancer predisposition, that are due to a mutation in a tumor suppressor gene, have been tested with the Apoptin/UV assay as yet. There is however no reason to assume that the same phenomenon will not be observed in other cancer-prone cells. A similar diagnostic test for predicting cancer-proneness can also be carried out by using X-ray treatment instead of UV irradiation.

The invention also allows us to obtain more information on the molecular basis of cancer-proneness and its relationship with certain stress-responses, such as Enhanced Reactivation (ER) (Abrahams et al., 1996). Enhanced Reactivation is one of the reactions of normal (human) cells to certain DNA-damaging agents, and appears to reflect the cells' susceptibility to oncogenic transformation. The invention will be explained in more detail in the following experimental part. This only serves for the purpose of illustration and should not be interpreted as a limitation of the scope of protection.

Experimental Part

Cells and Cell Culture Conditions

Rat embryo fibroblasts (REF) were prepared from 14-day-old rat embryos. The cells were thawn from liquid nitrogen, cultured in DMEM supplemented with 10% fetal calf serum, and transfected with plasmid DNA at cell passage 2. Mouse embryo fibroblasts (MEF) were prepared from p53+/+ mice or from p53−/− knock-out mice (Tyler Jacks, 1994 and 1996; Tyler Jacks et al., 1994). The cells were grown on Corning dishes in F15 medium supplemented with 10% fetal calf serum. P19 cells are derived from a mouse embryonal carcinoma/teratocarcinoma (Burney et al., 1982). The cells were grown on gelatinized Petri dishes in DMEM supplemented with 8% fetal calf serum. BRK/xho cells are prepared from baby rat kidney cells, by transforming with the adenovirus type 5 E1 region (Schrier et al., 1983). The cells were cultured in DMEM supplemented with 1.0% fetal calf serum. Human diploid foreskin fibroblasts VH10 and VH25 (Klein et al., 1990) were grown in Dulbecco's modified Eagle medium (DMEM) supplemented with 10% fetal-calf serum. Primary cultures of human epidermal keratinocytes (FSK-1) were initiated in complete medium as described (Rheinwald and Green, 1975), with minor modifications according to M. Ponec et al., 1981, and cultured in keratinocyte serum-free medium (KSFM) afterwards. For the experiments described here, passage number 3 was used. F9605 cells are diploid fibroblasts which are p16−/−, derived from patients with dysplastic nevus sydrome (DNS), which is postulated to be a precursor of familial a-typical multiple mole-melanoma (FAMMM) syndrome (Gruis et al., 1995). The cells were grown in DMEM with 10% fetal calf serum. GM1492 cells are human diploid fibroblasts, which do not express p53 and are derived from patients with Bloom's Syndrome, an autosomal recessive disorder with a high cancer incidence (Van Laar et al., 1994) The cells were grown in DMEM containing 10% fetal calf serum. LF2675T are diploid skin fibroblasts from patients with Li-Fraumeni syndrome, (LFS). This disease is characterized by a germline mutation in one allele of the p53 gene and an early onset of various types of cancer (Srivastava et al., 1990; Abrahams et al., 1996). The cells were grown in DMEM supplemented with 10% fetal calf serum. 401 cells are diploid skin fibroblasts from individual of Lynch type 2 syndrome family with a high incidence of various types of cancer. The cells were derived from an individual who died of breast cancer (Abrahams et al., 1996). The cells were grown in DMEM supplemented with 10% fetal calf serum. All culture media were obtained from GIBCO/BRL and contained the antibiotics penicillin and streptomycin.

Irradiation of the Cell Cultures

The conditioned medium was removed from the cultures and the cells were rinsed twice with PBS. After removal of the PBS, the cultures were UV-irradiated as described previously (Abrahams et al., 1984), or treated with X-rays (5 gray) by using an Andrex 225 SMART (Andrex St, Copenhagen) at 200 KV, 4 mA with a 1-mm Al filter. Dose and dose rate were monitored with a PTW dosimeter. After UV treatment, conditioned medium was returned, and the cultures were incubated at 37° C.

Plasmids

The expression plasmid pCMV-VP3 contains the CAV DNA sequence encoding the apoptin protein exclusively (nt 427–868; Noteborn et al., 1991, Noteborn and De Boer, 1996), and plasmid pCMV-des encodes desmin, a structural protein of muscle cells (Menke et al. 1997). Plasmid pCMV-neo is used as the "empty" negative control for plasmids encoding gene products with a potential effect on the apoptin-induced apoptosis. All expressed genes are under the regulation of the cytomegalovirus (early) enhanced promoter. Plasmid SV40 contains the SV40 origin-defective (ori-) early-region clone including both SV40 large T antigen- and small T antigen-coding regions regulated by their own promoter (Dinsart et al., 1984). The plasmid pR-s884 expresses a complete SV40 large T antigen and a truncated small T antigen under the transcriptional control of the long terminal repeat (LTR) of Rous sarcoma virus (RSV; De Ronde et al., 1989; Smits et al., 1992). The plasmid PR-SVt contains cDNA sequences coding for the SV40 small T gene that was fused to the RSV LTR (Philips and Bundell, 1988).

The expression plasmid 21EcoA, which consists of the murine H-2Kb histocompatibility antigen gene/promoter regions (Mellor et al., 1982) and pBr327 sequences is a gift from Prof Dr Frank Grosveld, Erasmus University, Rotterdam, The Netherlands. The plasmid 21EcoA contains a Not1 within the first exon of the H-2Kb gene, which enables the integration of a foreign gene becoming regulated by the H-2Kb promoter. The BamH1 fragment containing the sequences encoding apoptin was isolated from pCMV-VP3 and cloned an the Not1 site of 21EcoA plasmid by using Not1-BamHI linkers. The final plasmid containing the apoptin gene under the regulation of the H-2Kb promoter was called p21EcoA-VP3. Subsequently, the EcoR1-site next to the apoptin gene was deleted by linearization of plasmid p21EcoA-VP3 at this specific EcoRI site, and treatment with Klenow polymerase treatment. The plasmid is called p21EcoA-Vp3-Eco. The DNA fragment containing the H-2kB expression unit with the apoptin gene was separated from the procaryotic DNA sequences by means of EcoRI digestion and agarose-gel electrophoresis. Plasmid DNA was purified by centrifugation in a CsCl gradient and column chromatography in Sephacryl S500 (Pharmacia, Sweden).

Transient Transfection

The cells were transfected in monolayed cultures with transfection agent DOTAP (Boehringer, Mannheim, FRG) essentially as described by Fischer et al., 1996, or transfected with plasmid DNA by calcium-phosphate precipitation as described by Graham and Van der Eb (1973).

Indirect Immunofluorescence

All cells were grown on glass microscope slides. The slides were either uncoated (VH10, VH25), or coated with 3-amino-propyltriethoxysilane (TESPA; FSK-1). The cells were fixed with 80% acetone for 10 min at room temperature, and used for indirect immunofluorescence as described (Van den Heuvel, 1990). To demonstrate the presence and/or cellular localization of apoptin in transfected cells, mouse monoclonal antibody (Mab) CVI-CAV-85.1 (85.1; Noteborn et al., 1991); for human desmin the mouse Mab 33 (Monosan, Uden, The Netherlands); for SV40 T antigens Pab 419, kindly provided by Dr A.-G Jochemsen, University of Leiden, The Netherlands, was used. Fluorescein isothiocyanate-labeled goat anti-mouse antibody (Jackson Immunoresearch Laboratories Inc., West grove Pa., USA) was used as second antibody. Nuclear DNA was stained with 2,4-diamino-2-phenylindole (DAPI).

The Generation of Transgenic-apoptin Mice

For the generation of transgenic-apoptin mice, fertilized oocytes from the FVB mouse strain and mice from the murine strain were used as fosters. The micro-injections were carried out in the male pronuclei according to Brinster et al. (1981). Per micro-injection 500 copies of the EcoR1 DNA fragment, derived from plasmid p21EcoA-Vp3-Eco, containing the required H-2Kb transcription unit and the complete apoptin gene was injected.

Results and Discussion

Apoptin Induces Apoptosis in Rodent Transformed Cells but not in Normal Embryonic Cells. To examine whether apoptin fails to induce apoptosis in normal embryonic rodent cells, cultures of mouse embryo cells and rat embryo cells were transiently transfected with a plasmid encoding apoptin. As a negative control, cells were transfected with a plasmid encoding desmin, which does not have aoppotfic activity. Cells expressing apoptin were screened via indirect immunofluorescence with Mab 85.1, and cells expressing desmin with mouse Mab 33. Induction of apoptosis in apoptin- or desmin-positive cells was analyzed with the help of DAPI, which causes a regular staining in intact nuclei, but an irregular and/or weak staining in apoptotic nuclei. Five days after transfection around 10–20% of the desmin-positive cells were apoptotic, which is the basal level most likely due to the transfection event (data not shown, Menke et al., 1997, Danen-van Oorschot, 1997a). Two, 3, 4 or 5 days after transfection the percentage of apoptotic apoptin-positive cells did not significantly exceed the percentage of apoptotic cells observed in the desmin-positive cultures, indicating that apoptin does not induce apoptosis in normal embryonic cell cultures. Transient transfection of transformed mouse/rat embryonic or baby rat kidney cells with the plasmid encoding apoptin proved that apoptin is able to induce apoptosis in these cells. The results of apoptin expression in "normal" embryonic rodent versus transformed rodent cells are shown in FIG. 1. These data show that apoptin fails to induce apoptosis in normal adult and embryonic rodent cells, but does induce apoptosis in the virally transformed derivatives, at least in cell culture conditions.

Co-expression of SV40 Large T Antigen and Apoptin Results in Apoptin-induced Apoptosis in Normal Human Diploid Cells We have examined the effect of expression of transforming genes on apoptin-induced apoptosis in normal human cells derived from healthy individuals. To that end, human VH10 diploid fibroblasts and FSK-1 diploid keratinocytes were transiently co-transfected with plasmid pCMV-VP3 encoding apoptin and either plasmid pSV40 encoding both SV40 large T and small T antigen, pR-s884 encoding large T antigen, pR-Svt encoding small T antigen, or the negative-control plasmid pCMV-neo. By indirect immunofluorescence, the cells were analysed for apoptin-induced apoptosis. Both normal VH10 and FSK-1 cells did not undergo apoptosis when apoptin was transfected with the control plasmid. The results showed, as expected, that expression of apoptin alone is not able to induce apoptosis in normal human diploid cells, confirming the data described by Danen-Van Oorschot (1997). However, normal diploid human fibroblasts and keratinocytes expressing both apoptin and SV40 large T antigen, alone or together with small T antigen, underwent apoptin-induced apoptosis (FIG. 2). The rate of apoptosis induction was considerably increased in the presence of the viral transforming genes. Co-expression of the SV40 small T antigen with apoptin did not result in induction of apoptosis by apoptin. The transition of the normal cells, from apoptin-resistance to apoptin-susceptibility, can probably be explained by the fact that the apoptin protein translocates from a cytoplasmic localization to a nuclear localization. This transition becomes apparent already approximately 2 days after transfection of the SV40 plasmids (FIG. 3). One can conclude that an event takes place, in this example due to expression of a transforming product from a DNA-tumor virus, which results in the translocation of apoptin from the cytoplasm to the nucleus, which is followed by induction of apoptosis.

Co-expression of SV40 Large T Antigen and Apoptin Results in Apoptin-induced Apoptosis in Normal Rodent Diploid Cells Next, we have examined the effect of co-expression of transforming genes and apoptin on apoptosis induction in normal mouse embryo fibroblasts (MEF) derived from p53+/+ mice or from transgenic p53-/- mice. Both types of transiently transfected MEFs co-expressing the transforming SV40 large T gene with or without small T antigen in combination with apoptin, underwent very fast apoptosis, whereas MEF expressing apoptin together with a control plasmid or with a plasmid encoding the non-transforming small T antigen, did not result in apoptin-induced apoptosis. The results are shown in FIG. 4. Immunofluorescence analysis also revealed that co-expression of apoptin and SV40 large T antigen resulted in the cellular translocation of apoptin. In the examined MEFs apoptin is situated in the cytoplasm. Upon SV40 large T antigen expression, apoptin enters the nucleus, followed by the induction of apoptosis. As comparison, the percentage of apoptin-positive transformed mouse cells is also given in FIG. 5.

These results indicate that apoptin does not induce apoptosis in both p53+/+ and p53-/- mouse fibroblasts, but does so upon expression of a transforming protein. This information is important since it is known that "normal" p53-/- cells are very susceptible to spontaneous transformation and easily progress to more highly transformed phenotypes. Loss of p53 alone, however, is not sufficient to create a transformed character. Furthermore, this finding shows that apoptin can induce apoptosis upon expression of a transforming protein in other mammalian cells than human cells.

Co-expression of SV40 Large T Antigen and Apoptin Results in Apoptin-induced Apoptosis in Normal Diploid Cells Derived from Cancer-prone Human Individuals By means of transient transfection and immunofluorescence we have also examined the effect of apoptin in the normal fibroblasts F9605 and GM1492 which are derived from individuals who show an increased cancer incidence due to a genetic defect. Apoptin is not able to induce apoptosis in normal diploid cells from these cancer-prone individuals. However, upon expression of SV40 large T antigen, apoptin induces apoptosis (FIG. 6) after entering the nucleus (data not shown). These data confirm that diploid cells, from hereditary cancer-prone syndromes are not susceptible to apoptin, whereas they become so when they express a transforming gene. Thus, diploid cells from such hereditary syndromes are identical to "normal" diploid human cells in this assay.

The Effect on Induction of Apoptosis of Covalent Linkage of a SV40 Large T Antigen Nuclear Localization Signal to the Apoptin Protein Next, we have examined whether expression of a chimeric protein consisting of apoptin and the nuclear localization signal of SV40 LT antigen (amino acids N-Proline-Proline-Lysine-Lysine-Lysine-Argenine-Lysine-Valine-C (SEQ ID NO:1) of SV40 large T antigen covalently linked to the N-terminus of apoptin) results in the induction of apoptosis in non- and transformed human cells. The chimeric protein is called NLS-apoptin. To that end, non-transformed VH 10 human fibroblasta and transformed human osteosarcoma-derived Saos-2 cells (Danen-van Oorschot et al., 1997) were transfected with a plasmid encoding the chimeric protein NLS-apoptin. In both cell types, expression of NLS-apoptin resulted in the nuclear localization of apoptin and induction of apoptosis. Expression of the non-apoptotic protein Green Fluorescent Protein (GFP); (Pines, 1995) covalently linked to the NLS entered the nucleus, which did not result in the induction of apoptosis. These data prove that a modified apoptin enabling its nuclear localization in a cell-transformed-independent manner, will be able to translocate into the nucleus, followed by induction of apoptosis. A fusion product of the first N-terminal 69 amino acids of apoptin and the non-apoptotic GFP protein does not result in induction of apoptosis, and which coincides with the fact that this chimeric protein does not enter the nucleus (Noteborn and Pietersen, 1998). Now we have covalently linked the 8 amino acids of the NLS to the N-terminus of the apoptin fragment consisting of the amino acids 1–69 (NLS-apoptin/1–69). Transfection of both non-transformed VH10 cells and tumorigenic human cells (such as human osteosarcoma-derived Saos-2 cells) with a plasmid encoding the NLS-apoptin/1–69 resulted in the nuclear localization of the NLS-apoptin/1–69 followed by induction of apoptosis. These data indicate that besides the C-terminal part of apoptin, also the N-terminal part (1–69 a.a.) does so, when it is translocated into the nucleus. In these experiments, as expected, the NLS-GFP was translocated into the nucleus but did not result in the induction of apoptosis.

Normal Diploid Cells from Cancer-prone Individuals Undergo Apoptin-induced Apoptosis after UV-radiation We have also examined the effect of UV-irradiation on apoptosis induction by apoptin on diploid cells. Diploid fibroblasts derived from healthy persons (VH25) or from individuals with a cancer-prone syndrome (LF2675T cells from a Li Fraumeni Syndrome patient, and 401 cells from a Lynch Type 2 Syndrome patient) were transiently transfected with a plasmid encoding apoptin. Before transfection, part of the cells was UV-radiated. As negative control, the cells were transfected with a plasmid encoding the protein desmin.

All 3 cell types, VH25, LF2675T and 401, did not reveal apoptin-induced apoptosis without UV irradiation. In combination with UV irradiation, however, the LF2675T and 401 cells, but not the VH25 cells, underwent apoptin-induced apoptosis very rapidly. Although we have no explanation for this phenomenon, it appeared that it correlates with another cellular property. Diploid cells from patients who are cancer-prone due to a germline mutation in a tumor suppressor gene, show an unexpected reaction to UV irradiation. When normal diploid fibroblasts are treated with UV or another DNA damaging agent, they react with a large variety of transient responses, including activation of signal transduction pathways, induction of expression of a variety of genes, inhibition of cellular DNA replication and activation of SOS-like phenomena such as Enhanced reactivation (ER) and Enhanced mutagenesis (EM). Abrahams et al. (1996) have found that normal diploid fibroblasts from patients with a. hereditary cancer predisposition due to a germline mutation in a tumor suppressor gene, show the same responses to UV irradiation as cells from normal individuals, except for one response: Enhanced reactivation. The ER response in cells from these patients is much higher than in cells from normal individuals, hence these patient cells are called ERsuper (+). The molecular-biological basis of the ER phenomenon is still unclear. The detection of ER is a time-consuming approach, as it is based on the measurement of the (enhanced) survival of a UV-irradiated virus in UV-damaged (or X-ray damaged) cells, compared to the survival in non-damaged cells. An assay based on apoptin-induced apoptosis upon UV-radiation is considerably simpler and faster (see below) . The fact that apoptin becomes active in cancer-prone cells upon UV-radiation makes it also possible to study the ER proces. There is evidence to indicate that ER plays an important role in the process of cancer induction by DNA-damaging agents.

Normal Diploid Cells from Cancer-prone Individuals Undergo Apoptin-induced Apoptosis after X-ray Treatment Next, we have also examined the effect of X-ray treatment on the apoptosis induction by apoptin on human diploid cells. Diploid fibroblasts derived from healthy individuals (VH10) or from persons with a cancer-prone syndrome such as LF2675 and 401 cells were transfected with a plasmid encoding apoptin. Before, transfection, part of the cells was treated with X-rays (dose; 5 gray). As negative control, the cells were transfected with a plasmid encoding the protein desmin.

As expected, all analysed non-irradiated cells of the cell lines: VH10, LF2675 and 401, did not show apoptin-induced apoptosis. In combination with X-ray treatment, however, the cell lines derived from the cancer-prone individuals underwent apoptosis, whereas the ones derived from healthy persons did not. Five days after transfection, the majority of these X-ray-treated apoptin-positive cancer-prone cells had become apoptotic. The cells treated with X-rays and expressing the non-apoptotic agent desmin, did not undergo apoptin-induced apoptosis.

These results imply that treatment with X-rays, causing DNA-damage such as the above described UV-C treatment, results in the induction of apoptosis by apoptin in normal non-transformed human cells.

Diagnostic Assay for Cancer-inducing Genes Based on Apoptin-induced Apoptosis

Danen-Van Oorschot et al. (1997a) have reported that the cellular localization of apoptin is different in tumorigenic/transformed human cells in comparison to the localization in normal non-transformed cells. Furthermore, accumulation of apoptin in the nucleus correlates with apoptosis induction, whereas cytoplasmic localization correlates with cell viability and normal proliferative capacity.

Based on the present report, we are able to develop a diagnostic assay for the identification of cancer-inducing and/or transforming agents or genes. A first type of assay consists of transfecting "normal" cells, for instance from human or rodent origin, with a plasmid encoding apoptin, or infecting the cells with viral vectors expressing apoptin, together with a plasmid encoding a putative transforming/cancer-inducing gene. Subsequently, the cells will be examined, (1) for the ability to undergo apoptosis by the apoptin gene and (2) for a shift in the localization of apoptin from the cytoplasm to the nucleus. The intracellular localization of apoptin can be determined, using an immunofluorescence assay with monoclonal antibodies specific for apoptin, such as CVI-CAV-85.1. If the percentage of apoptosis in normal cells co-expressing apoptin and the putative transforming/cancer-inducing gene is significantly higher than in apoptin-positive control cells expressing a control plasmid, one can conclude that the analysed gene may indeed have transforming/cancer-inducing activity.

A second example of a diagnostic test is based on the treatment of cultured normal diploid cells with a putative carcinogenic agent. The agent can be added, for instance, to the culture medium for various lengths of time. Subsequently, the cells are transfected with a plasmid encoding apoptin or infected with a viral vector expressing apoptin. This approach can also be carried out by first transfecting/infecting the normal cells, and then treating the cells with the agent to be tested. The subsequent steps of the assay are the same as described for the first type of diagnostic assay.

Diagnostic Assay for Cancer-proneness

The data presented in this report allow us to develop an assay to determine whether an individual with an unknown cellular/genetic background, is cancer-prone compared to normal healthy persons. Normal diploid cells from a cancer-prone individual are insensitive to apoptin-induced apoptosis, but become so after treatment with UV- or X-rays or another DNA damaging agent. Below, an example of such a diagnostic assay is described based on the effect of UV-irradiation. This assay can also be carried out with other mutagenic/carcinogenic agents.

Primary normal diploid cells are isolated from a skin biopsy of the individual to be tested and cultured in a suitable medium. Next, the cells are irradiated with UV and subsequently transfected with a plasmid encoding apoptin, or infected with a viral vector expressing apoptin, or the cells are first transfected/infected and then irradiated. In parallel, diploid cells from a normal healthy individual will be used as a control. By using an indirect immunofluorescence assay based on apoptin-specific Mab's, the cells are analysed for the presence of apoptin in the nucleus and/or for undergoing apoptosis. If the percentage of cells undergoing apoptosis among the apoptin-positive UV-treated cells is significantly higher than the percentage of apoptosis in UV-treated cells of a normal individual, this will be strong evidence that the individual from whom the cells are isolated, will be cancer-prone.

Use of Apoptin Proteins in Pharmaceutical Formulations for Anti-cancer Therapy

On the basis of the above mentioned results one can also develop methods to apply apoptin in anti-cancer therapy, not as a gene (DNA) but as a protein. Apoptin is a comparatively small protein, which makes it feasible to introduce it into cells as a protein. (If fragments of the apoptin protein still have the desired apoptotic effect on cancer cells, we will use protein fragments instead of the intact protein). Our aim is to develop effective pharmaceutical formulations that ensure stability of the active component (=apoptin or a fragment thereof) and, if possible specificity for the tumor cell to be targeted. The neoplasias that we hope to treat with suitable apoptin-containing formulations, both curative and preventive, include: hereditary forms of colorectal cancer (Familial adenomatous polyposis (APC) and hereditary non-polyposis colorectal cancer (HNPCC), cancer of the liver (or other organs that can be treated with perfusion techniques), leukemias and lymphomas (to be treated via the blood circulation), skin tumors and possibly lung tumors (via the respiratory tract).

The Construction and Analyses of an Expression-plasmid for the Generation of Transgenic-apoptin Mice The fact that we have now observed that apoptin fails to induce apoptosis in cultured murine embryonic fibroblasts, let us conclude that apoptin may also be expressed in the intact embryo and adult mice without causing toxicity, at least embryos of a not too early stage of embryonic development. We have chosen an expression system based on the murine H-2Kb transcription unit, which allows constitutive expression of foreign genes during embryogenesis and at adult stages in various organs (Drezen et al., 1992; Morello et al., 1986). Therefore, we have constructed the expression plasmid p21EcoA-Vp3-Eco, which expresses apoptin under regulation of the murine H-2Kb promoter. Futhermore, the expression vector contains the other H-2Kb elements, which will allow expression of the apoptin gene. FIG. 8 shows a schematic representation of the transgenic-apoptin expression vector p21EcoA-Vp3-Eco. By means of transient transfections of transformed Saos-2 cells with the plasmid p21EcoA-Vp3-Eco we were able to prove that apoptin indeed could be expressed in the context of the H-2Kb sequences. Futhermore, the expressed apoptin resulted in the induction of apoptosis to a similar extent as apoptin expressed by means of the plasmid pCKV-VP3 (see FIG. 9). These results imply that the used expression vector p21EcoA-Vp3-Eco expresses apoptin in such a way that transformed cells will undergo apoptosis.

The Generation of Transgenic-apoptin Mice

In total 300 fertilized oocytes were micro-injected with a DNA fragment comprising of the H-2Kb transcription unit and the apoptin gene and transferred to 11 foster mice. In total we had gathered a progeny of 51 newborn mice.

By means of Southern-blot analysis (Southern, 1975) of BamHI- or XbaI-digested mouse-tail DNA using a 32P-labeled DNA fragment consisting of the complete VP3 gene, it was shown that the apoptin-H-2Kb unit was integrated within the genomic DNA of in total 7 founder (FO) mice. All transgenic-apoptin mice were looking healthy. For unknown reasons, however, 1 transgenic-apoptin mouse died at an age of 5–6 weeks. The transgenic-apoptin mice were mated with FVB males or females. Tail DNA from the progeny was analysed for the presence of the apoptin gene using a polymerase chain reaction (PCR)-analysis using the primers P1 (5'CTCTCCAACAACATACT-CCACCCGG-3') (SEQ ID NO:2) and (CTTATACGCCTTTTT-GCGGTTCGGG-3') (SEQ ID (NO:3). From all F0 mice, we have got 1 or more trangenic-apoptin F1-mice (FIG. 10).

All mice of the F1-generation of the transgenic-apoptin animals were proven to be viable and thus far do not show any pathological defect, which might be correlated with the expression of apoptin.

By means of Northern-blot analysis (Noteborn et al., 1992) the expression of the apoptin gene could, as expected, be determined in various organs.

REFERENCES

Figure 1:
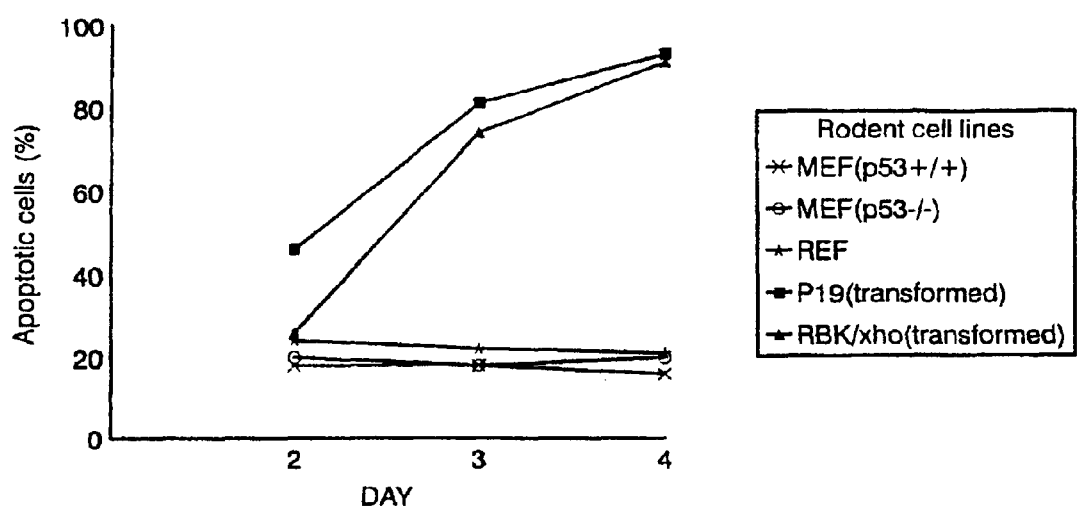
FIG. 1 shows the apoptin-induced apoptosis activity in "normal" rodent embryo fibroblasts versus cells of transformed rodent cell lines. The cells were transiently transfected with pCMV-VP3 . Subsequently, the cells were fixed at several time intervals after transfection and analysed by indirect immunofluorescence using the apoptin-specific Mab 85.1. The percentage of apoptin-positive cells that stained abnormally with DAPI is given as relative measure for the induction of apoptosis.
Figure 2:
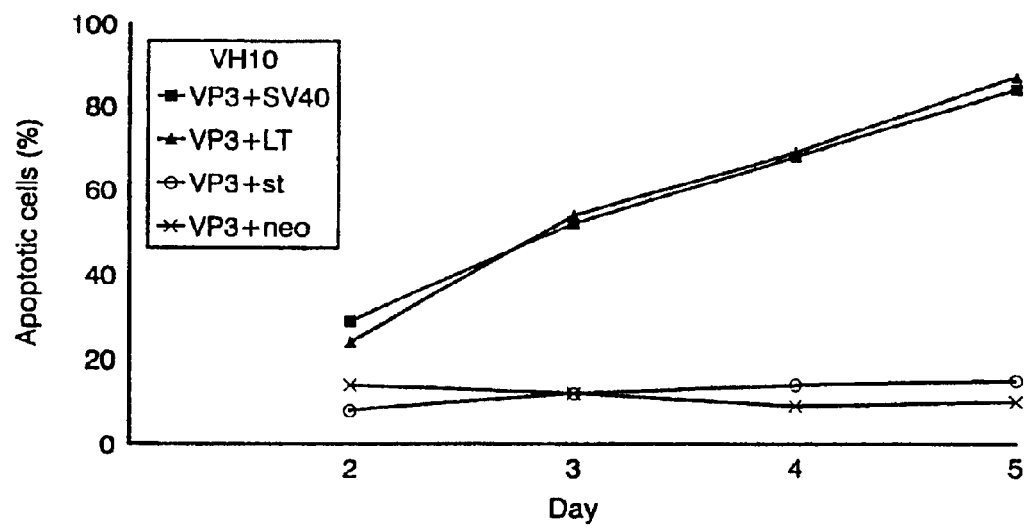
FIG. 2 shows the effect of SV40 large T antigen and/or small T antigen on apoptin-induced apoptosis in fibroblasts and keratinocytes from normal individuals. VH10 and FSK-1 cells were transiently transfected with plasmid pCMV-VP3 and pCMV-neo or pSV40 expressing SV40 large T and small T antigen, pR-s884 expressing SV40 large T antigen, and pR-SVt expressing the SV40 small t antigen. Subsequently, the cells were fixed at several time intervals after transfection and analysed by indirect immunofluorescence using the apoptin-specific Mab 85.1. The percentage of apoptin-positive cells that stained abnormally with DAPI is given as relative measure for apoptosis.
Figure 2:
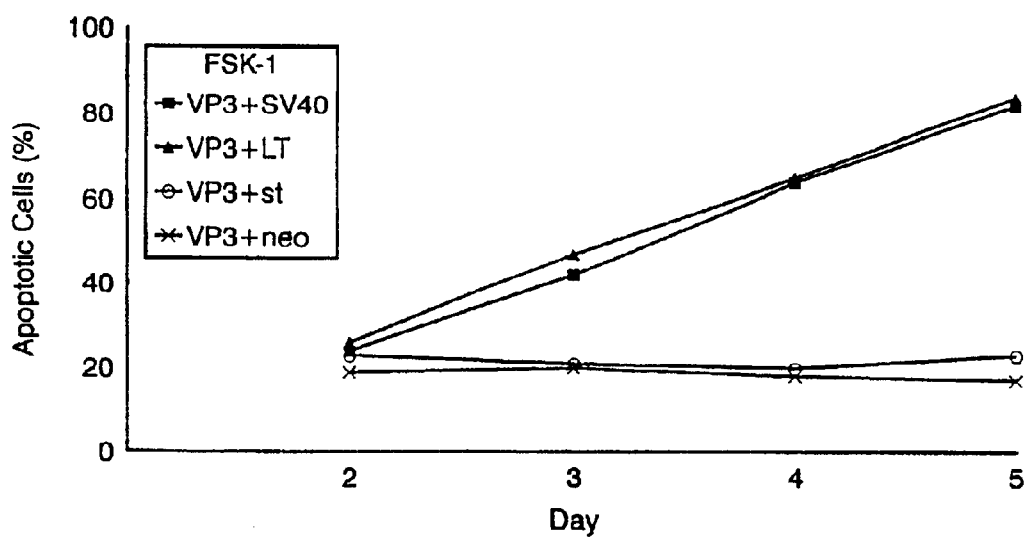
Figure 3:
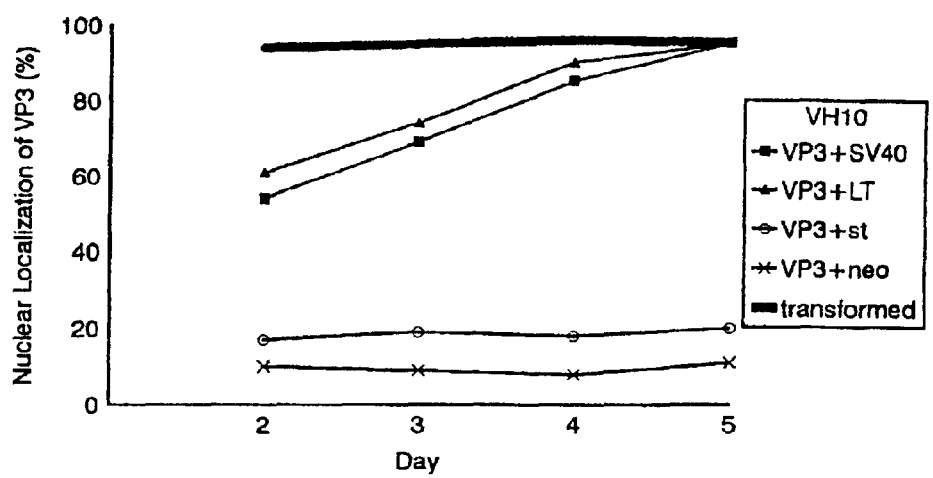
FIG. 3 shows the location of apoptin in normal human diploid cells expressing only apoptin or together with SV40 large T antigen and/or small T antigen. The same cells analysed in FIG. 2, regarding the induction of apoptosis were examined also for location of apoptin in the nucleus or cytoplasm. The percentage of apoptin-positive cells containing apoptin in the nucleus and still have not undergone apoptosis are given as relative measure of apoptin localization in the nucleus.
Figure 3:
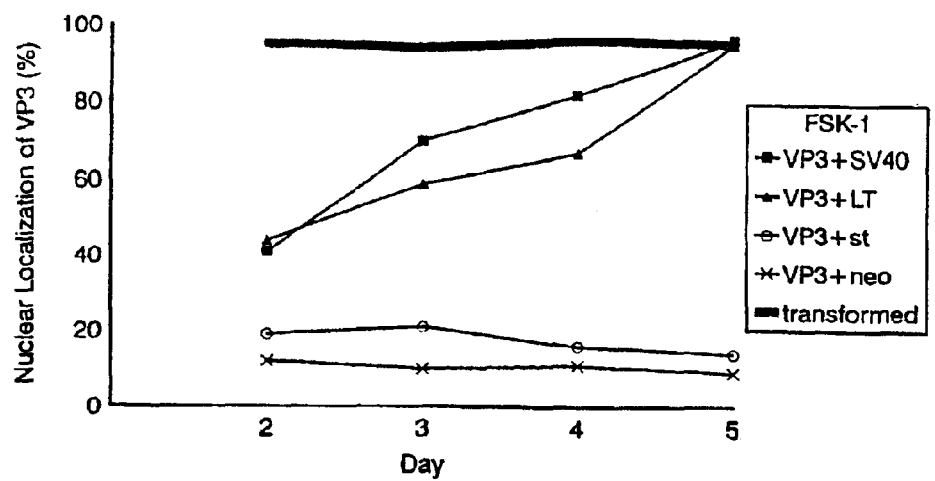
Figure 4:
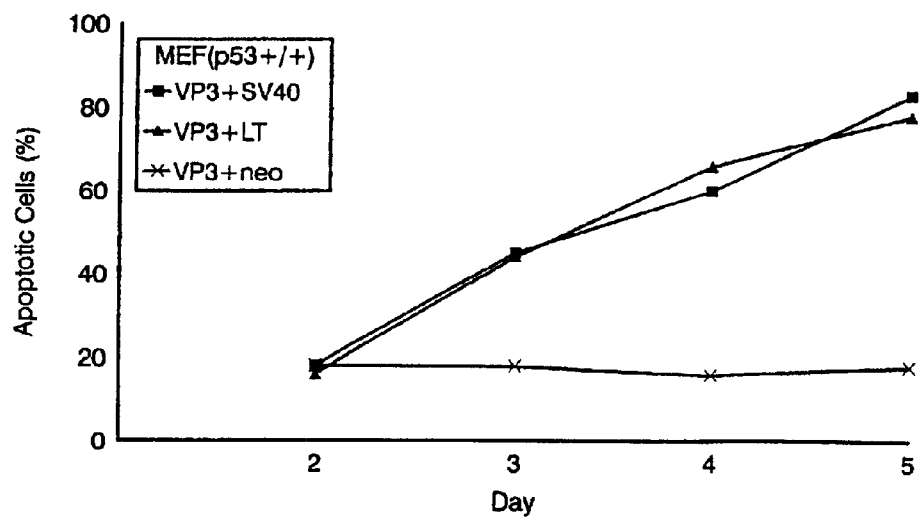
FIG. 4 shows the effect of SV40 large T antigen and/or small T antigen on apoptin-induced apoptosis in mouse fibroblasts, which are derived from normal p53+/+ mouse or from a transgenic p53−/− knock-out mouse. The cells were transiently transfected with plasmid pCMV-VP3, expressing apoptin and the control plasmid pCMV-neo or with pSV40 expressing SV40 large T antigen, pR-s884 expressing large T antigen, and pR-SVt encoding small T antigen. Subsequently, the cells were fixed at several time intervals after transfection and analysed by indirect immunofluorescence using the apoptin-specific Mab 85.1. The percentage of apoptin-positive cells that stained abnormally with DAPI is given as relative measure for apoptosis
Figure 4:
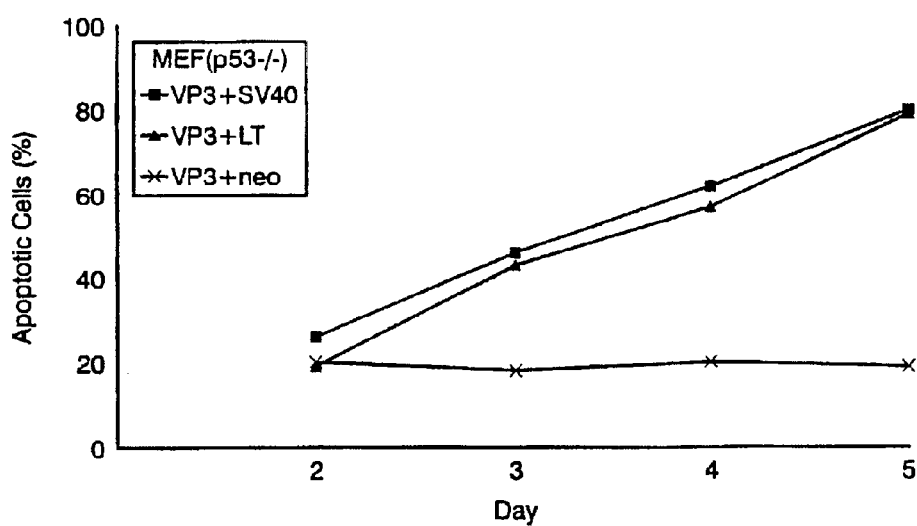
Figure 5:
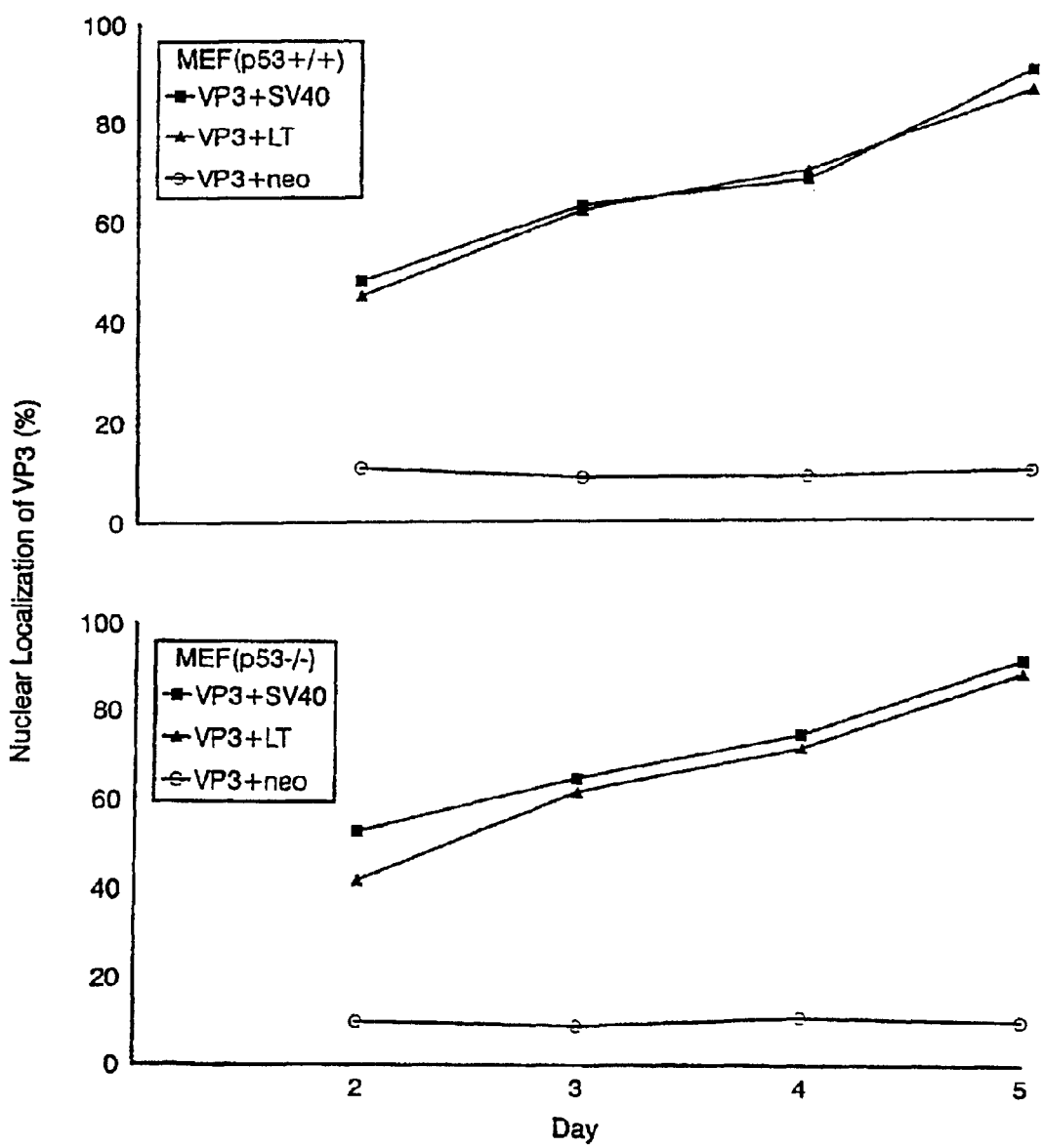
FIG. 5 shows the location of apoptin in mouse embryonic p53+/+ or p53−/− fibroblasts expressing only apoptin or together with SV40 large T antigen and/or small T antigen. The same cells were analysed in FIG. 4 regarding the induction of apotosis were now also examined for location of apoptin in the nucleus or cytoplasm. The percentage of apoptin-positive cells containing apoptin in the nucleus and still being apoptotic are given as relative measure of apoptin localization in the nucleus.
Figure 6:
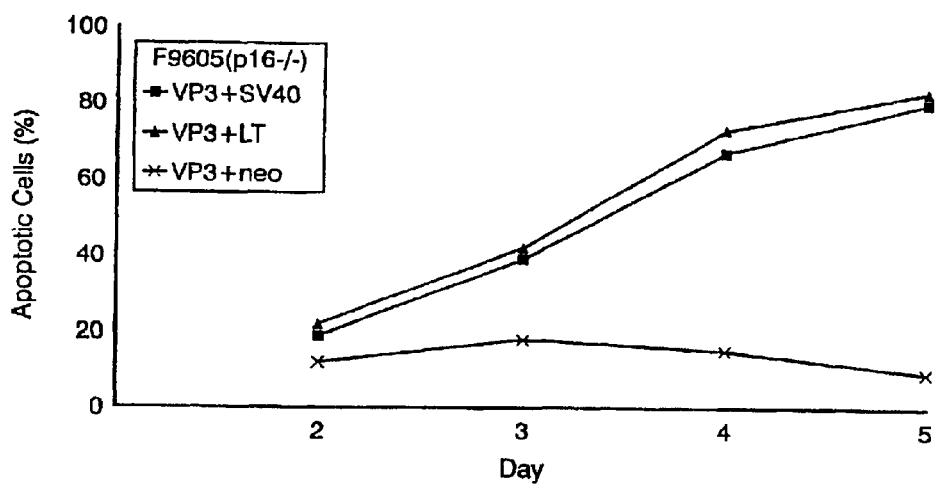
FIG. 6 shows the effect of SV40 large T antigen on apoptin-induced apoptosis activity in "normal" diploid human fibroblasts 9605 or G4905 derived from cancer-prone individuals. The cells were transiently transfected with pCMV-VP3 and pCMV-neo, or pSV40 expressing both large T and small T antigen of SV40, pR-s884 expressing large T antigen and pR-SVt expressing small T antigen. Subsequently, the cells were fixed at several time intervals after transfection and analysed by indirect immunofluorescence using the apoptin-specific Mab 85.1. The percentage of apoptin-positive cells that stained abnormally with DAPI is given as relative measure for apoptosis.
Figure 6:
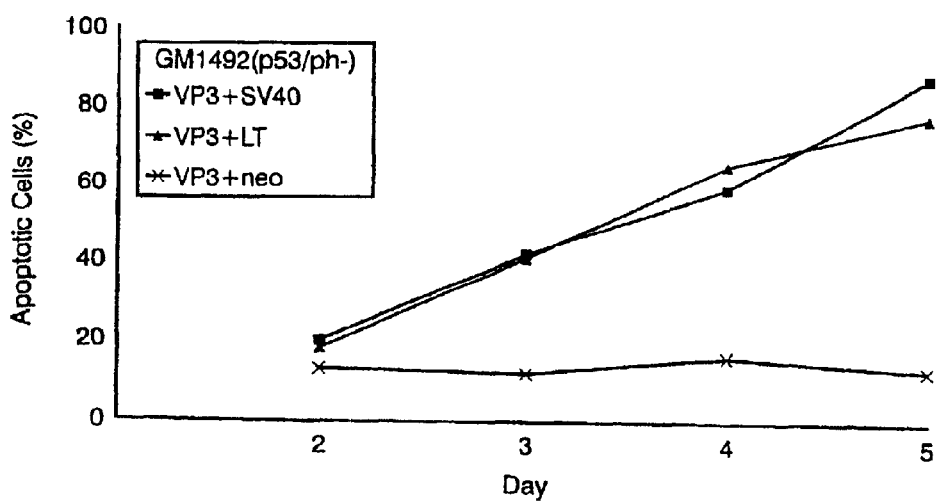
Figure 7:
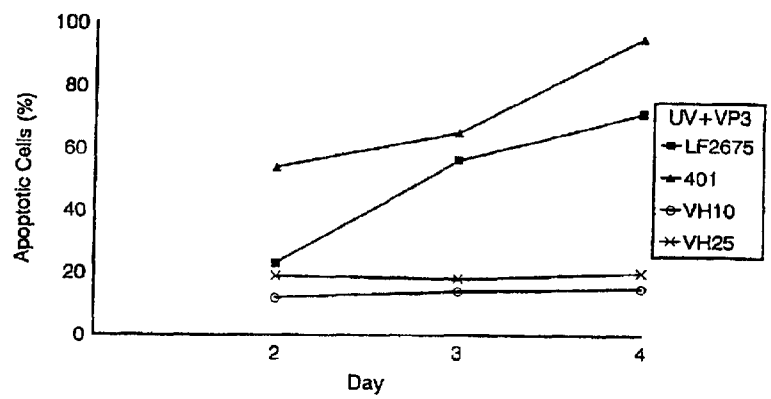
FIG. 7 shows the effect of UV-irradiation on apoptin-induced apoptosis in "normal" diploid fibroblasts derived from normal healthy individuals versus cancer-prone patients. The cells were mock-treated or treated with UV-light and subsequently transiently transfected with pCMV-VP3 or with pCMV-des. Finally, the cells were fixed at several time intervals after transfection and analysed by indirect immunofluorescence using the apoptin-specific Mab 85.1. The percentage of apoptin-positive cells that stained abnormally with DAPI is given as relative measure for apoptosis.
Figure 7:
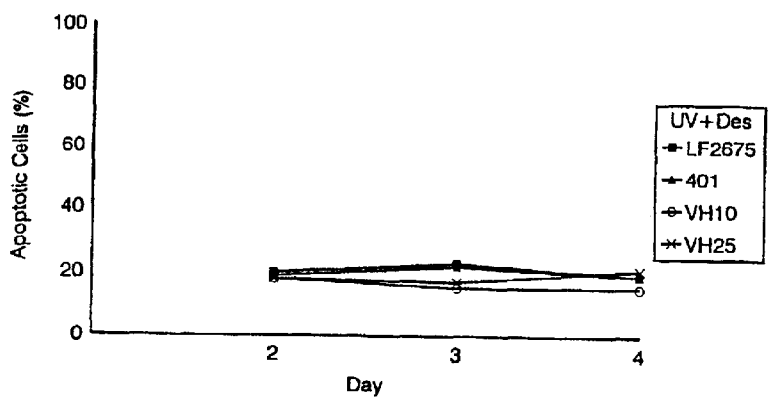
Figure 7:
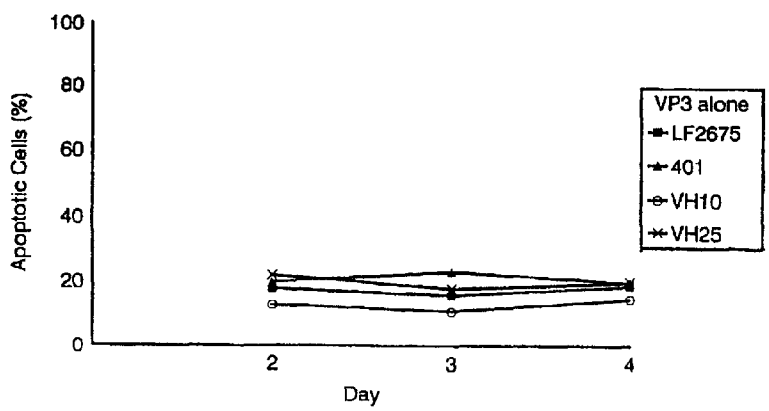
Figure 8:
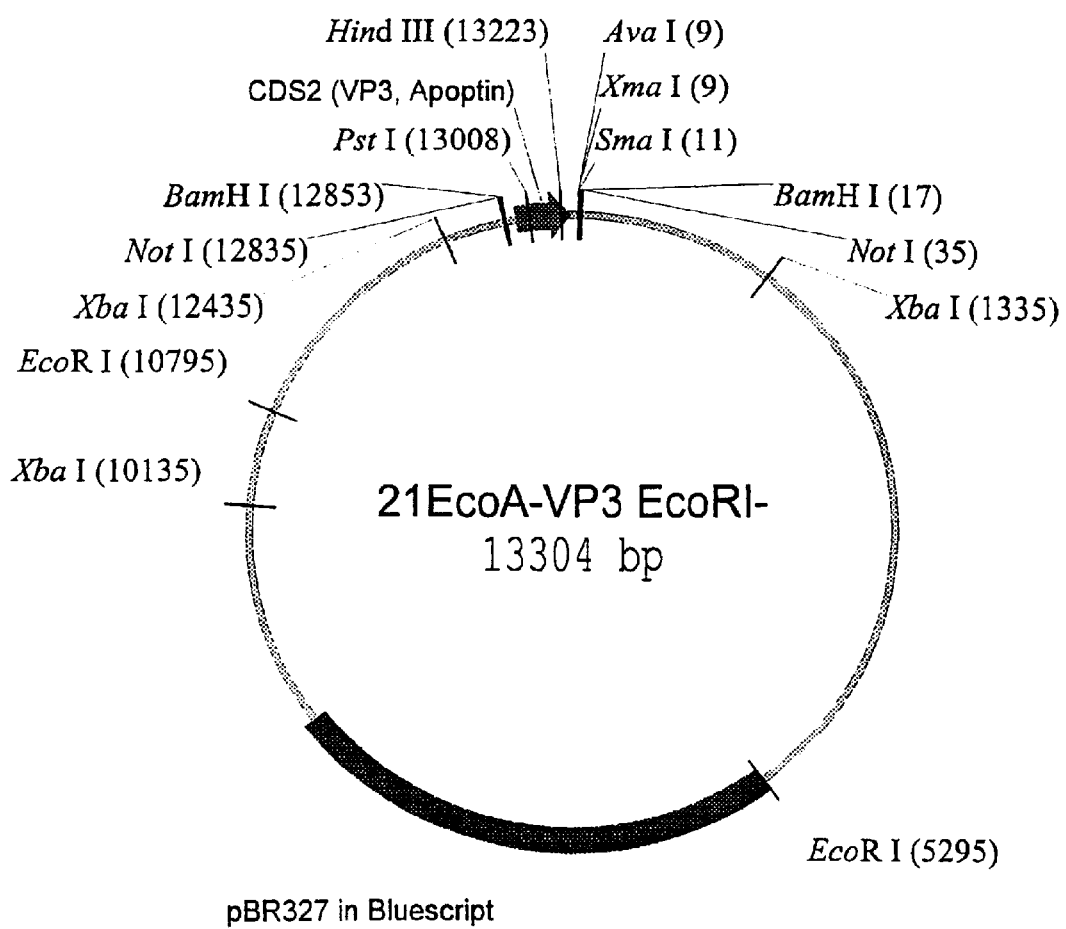
FIG. 8 shows a schematic representation of the transgenic-apoptin expression vector.
Figure 9:
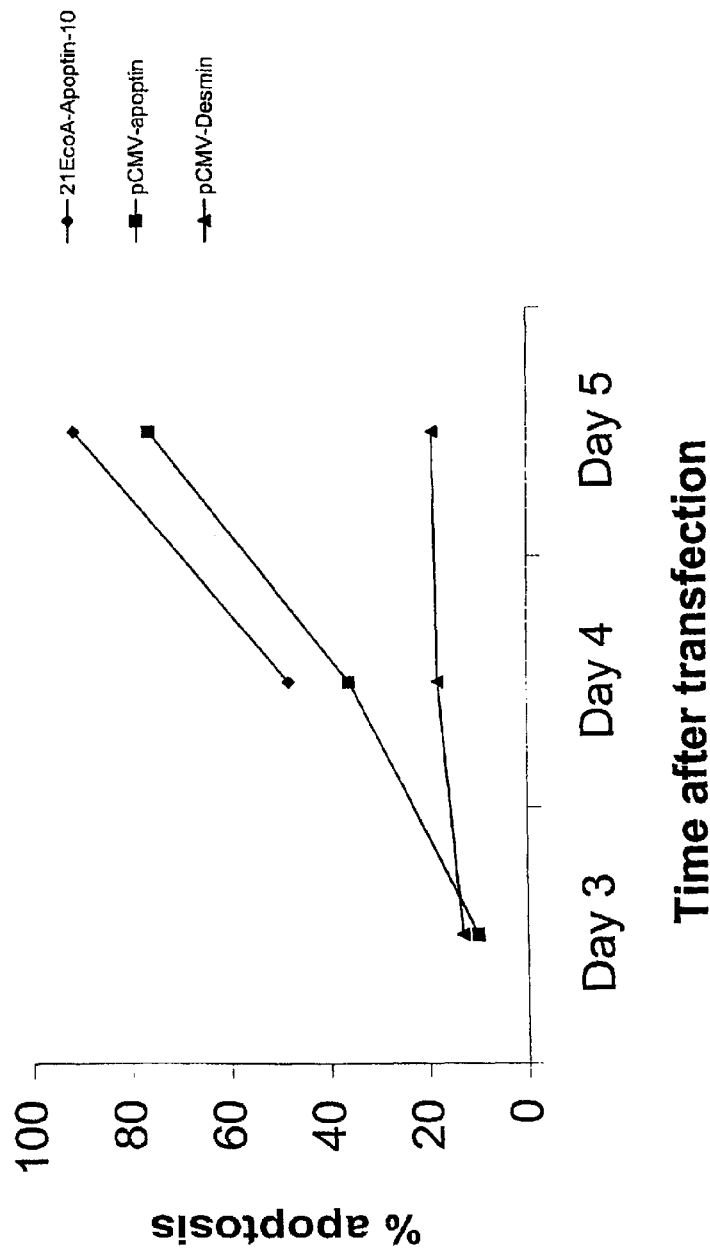
FIG. 9 shows the apoptin-induced apoptosis activity in Saos-2 cells. The cells were transiently transfected with p21EcoA-Vp3-Eco, pCMV-VP3 (both expressing apoptin) or with pCMV-des, expressing the non-apoptotic protein desmin. Subsequently, the cells were fixed at several time intervals after transfection and analysed by indirect immuno-fluorescence using the apoptin-specific Mab 8S.1. The percentage of apoptin-positive cells that stained abnormally with DAPI is given as a relative measure for the induction of apoptosis.
Figure 10:
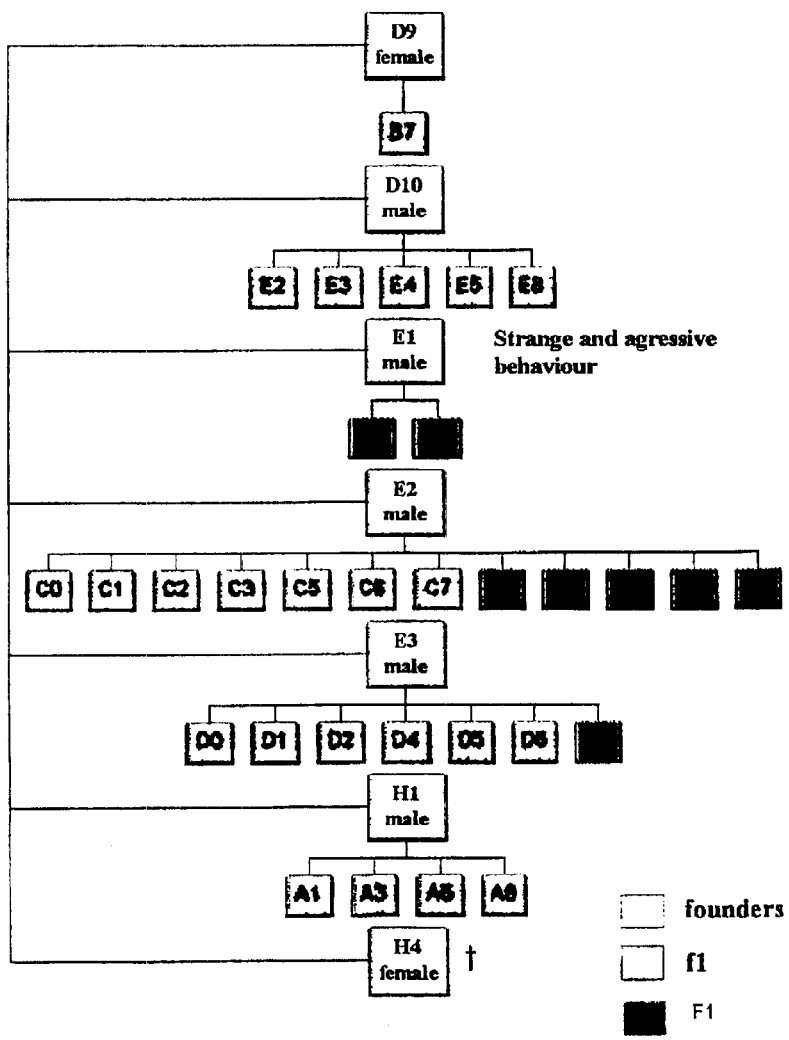
FIG. 10 Schematic representation of the pedigree of the VP3 (apoptin)-transgenic mice. The white-colored boxes are founder mice. The yellow- and green-colored boxes represent the progeny (F1) of the various apoptin-transgenic founders.

1. Abrahams, P. J., Huitema, B. A., and Van der Eb, A. J. (1984). Enhanced reactivation and enhanced mutagenesis of herpes simplex virus in normal human and xeroderma pigmentosum cells. Molecular Cellular Biology 4, 2341–2346. Abrahams, P. J., Houweling, A., and Van der Eb, A. J. (1992). High levels of enhanced reactivation of Herpes simplex virus in skin fibroblasts from various hereditary cancer-prone syndromes. Cancer Research 52, 53–57.
2. Abrahams, P. J., Houweling, A., Cornelissen-Steijger, P. D. M., Arwert, F., Menko, F. H., Pinedo, H. M., Terleth, C., and Van der Eb, A. J. (1996). Inheritance of Abnormal Expression of SOS-like Response in Xeroderma Pigmentosum and Hereditary Cancer-prone Syndromes. Cancer Research, 56, 2621–2625.
3. Bellamy, C. O C., Malcomson, R. D. G., Harrison, D. J., and Wyllie,H.1995. Cell death and disease: The biology and regulation of apoptosis. Seminars on Cancer Biology 6, 3–12.
4. Brinster, R. L., Chen, H. Y., and Trumbauer, M. E. (1981). Mouse oocytes transcribe injected Xenopus 5S RNA gene. Science 211, 396–398.
5. Danen-van Oorschot, A. A. A. M., Fischer, D., Grimbergen, J. M., Klein, B., Zhuang, S.-M., Falkenburg, J. H. F., Backendorf, C., Quax, P. H. A., Van der Eb, A. J., and Noteborn, M .H. M. (1997). Apoptin induces apoptosis in human transformed and malignant cells but not in normal cells. Proceedings National Academy Sciences, USA: 94, 5843–5847.
6. Danen-van Oorschot, A. A. A. M., Den Hollander, A., Takayama, S., Reed, J., Van der Eb, A. J., and Noteborn, M. H. M. (1997) BAG-1 inhibits p53-induced but not apoptin-induced apoptosis. Apoptosis, In Press.
7. Dinsart, C., Cornelis, J. J., Klein, B., van der Eb, A. J., and Rommelaere, J. (1984). Transfection with extracellularly UV-damaged DNA induces human and rat cells to express a mutator phenotype towards parvovirus H-1. Molecular Cellular Biology 4, 324–
8. Drezen, J. M., Nouvel, P., Babinet, C., and Morello, D. (1992). Different regulation of class I gene expression in the adult mouse and during development. The Journal of Immunology 149, 429–437.
9. De Ronde, A., et al. (1989). The SV40 small t antigen is essential for the morphological transformation of human fibroblasts. Virology 171, 260–263.
10. Duke, R. C., Ocjius, D. M., Young, J, D-E. (1996). Cell suicide in health and disease. Scientific American December 1996, 48–55.
11. Earnshaw, W. C., 1995. Nuclear changes in apoptosis. Current Opinion in Cell Biology 7, 337–343.

12. Fischer, D. F., Gibbs, S., Van de Putte, P., and Backendorf, C. (1996). Interdependent transcription control elements regulate the expression of the SPRR2A gene during keratinocyte terminal differentiation. Molecular and Cellular Biology 16, 5365–5374.
13. Graham, F. L. and Van der Eb, A. J. (1973). A new technique for the assay of infectivity of human adenovirus 5 DNA. Virology 52, 456–467.
14. Gruis, N. A. et al. (1995). Homozygotes for CDKN2 (P16) germline mutation in Dutch familial melanoma kindreds. Nature Genetics, 10: 351–353, 1995.
15. Hockenberry, D. M. (1994). Bcl-2 in cancer, development and apoptosis. Journal of Cell Science, Supplement 18, 51–55.
16. Jacks, T. Lessons from the p53 mutant mouse (1996). Journal of Cancer Research and Clininal Oncology 12.2, 19–27.
17. Jacks, T. (1994). Tumor spectrum analysis in p53-mutant mice. Current Biology 4, 1–7.
18. Kerr, J. F. R., Winterford, C. M., and Harmon, B. V. (1994). Apoptosis: Its significance in cancer and cancer therapy. Cancer 73, 2013–2026.
19. Klein, B., Pastink, A., Odijk, H., Westerveld, A., and Van der Eb, A. J. (1990). Transformation and immortalization of diploid Xeroderma pigmentosum fibroblasts. Experimental Cellular Research 191, 256–262.
20. Levine, A. J. (1997). P53, the cellular gatekeeper for growth and division. Cell 88, 323–331.
21. Lowe, S. W., et al. (1994). Abrogation of oncogene-associated apoptosis allows transformation of p53-deficient cells. Proceedings of the National Academy of Sciences, USA 91, 2026–2030.
22. Maniatis, T., Fritsch, E. F., and Sambrook, J. (1982). Molecular Cloning: A Laboratory Manual. CSHL Press, New York, USA.
23. McBurney, M. W. et al. (1982). Isolation of male murine embryonal carcinoma cells and their chromosome replication patterns. Developments in Biology 89, 503–508.
22. McDonell T. J., Meyn, R. E., Robertson, L. E. (1995). Implications of apoptotic cell death regulation in cancer therapy. Seminars in Cancer Biology 6, 53–60.
23. Menke, A. L., Shvarts, A., Riteco, N., Van Ham, R. C. A., Van der Eb, A. J., and Jochemsen, A. G. (1997). Wilms Tumor 1 (WT1) splice variants lacking the KTS induce apoptosis in p53-negative and p53-positive HepG2 cells. Cancer Research 57, 1353–1363.
24. Mellor, A. L., Golden, L., Weiss, E., Bullman, H., Hurst, Simpson, E., James, R. F., Townsend, A. R., Taylor, P. M., Schmidt, W., Ferluga, J., Leben, L., Santamaria, M., Atfield, G. Festenstein, H., Flavell, R. A. (1982). Expression of murine H-2Kb histocompatibility antigen in cells transformed with cloned H-2 genes. Nature 298, 529–534.
25. Morello, D., Moore, G., Salmon, A. M., Yaniv, M., and Babinet, C. (1986). Studies on the expression of an H-2K/human growth hormone fusion gene in giant transgenic mice. The EMBO Journal 5, 1877–1883.
26. Noteborn, M. H. M. and Pietersen, A. M. (1998). PCT application 98/00213 entitled Adenovirus vector.
27. Noteborn, M. H. M. (1996). PCT application WO 96/41191. Apoptin induces apoptosis in human transformed and malignant cells but not in normal cells as essential characteristic for the development of an anti-tumor therapy.
28. Noteborn and De Boer, G. F. (1996). Patent USA/no. 030, 335.
29. Noteborn, M. H. M., De Boer, G. F., Van Roozelaar, D., Karreman, C., Kranenburg, O., Vos, J., Jeurissen, S., Zantema, A., Hoeben, R., Koch, G., Van Ormondt, H., and Van der Eb, A. J. (1991). Characterization of cloned chicken anemia virus DNA that contains all elements for the infectious replication cycle. Journal of Virology 65, 3131–3139.
30. Noteborn, M. H. M., Hoeben, R. C., and Pietersen, A. (1997). A gene delivery vehicle expressing the apoptosis-inducing proteins VP2 and/or apoptin. European Patent Application no. 97201121.7
31. Noteborn, M. H. M., Todd, D., Verschueren, C. A. J., De Gauw, H. W. F. M., Curran, W. L., Veldkamp, S., Douglas, A. J., McNulty, M. S., Van der Eb, A. J., and Koch, G. (1994). A single chicken anemia virus protein induces apoptosis. Journal of Virology 68,. 346–351.
32. Noteborn, M. H. M., Kranenburg, O., Zantema, A., Koch, G., De Boer, G. F, and Van der Eb, A. J. (1992). Transcription of the chicken anemia virus (CAV) genome and synthesis of its 52-kDa protein. Gene 118, 267–271.
33. Paulovich, A. G., Toczyski, D., Hartwell, H. (1997). When checkpoints fail. Cell 88, 315–321.
34. Philips, B., and Rundell, K. (1988). Failure of semian virus 40 small t antigen to disorganize actin cables in nonpermissive cell lines. Journal of Virology 62, 768–775.
35. Pines, J. (1995). GFP in mammalian cells. Trends in Genetics 11, 326–327.
36. Ponec , M., Kempenaar, J. A., and De Kloet, E. R. (1981). Corticoids and cultured human epidermal keratinocytes: specific intra-cellular binding and clinical efficacy. Journal Investmental Dermatology 76, 211–214.
37. Reinwald, J. G. and Green, H. (1975). Cell 6, 331–343.
38. Sachs, L. and Lotem, J. (1993). Control of programmed cell death in normal and leukemia cells: New implications for therapy. Blood 82, 15–21.
39 Schrier, P. I., Bernards, R.., Vaessen, R. T. M. J., Houweling, A. and Van der Eb, A. J. (1983). Expression of classI major histocompatibility antigens switched off by highly oncogenic adenovirus 12 in transformed rat cells. Nature, 305, 771–775.
40. Smits, P. H. M. et al. (1992). Modulation of the human papillomavirus type 16 induced transformation and transcription by deletion of loci on the short arm of human chromosome 11 can be mimicked by SV40 small t. Virology 190, 40–44.
41. Southern, E. M. (1975). Detection of specific sequences among DNA fragments separated by gel electrophoresis. Journal of Molecular Biology 98, 503–517.
42. Srivastava, S., Zou. Z., et al. (1990). Germline transmission of a mutated p53 gene in a cancer-prone family with Li-Fraumeni syndrome. Nature 348, 747–749.
43 Steller, H. (1995). Mechanisms and genes of cellular suicide. Science 267, 1445–1449.
44. Telford, W. G., King, L. E., Fraker, P. J. (1992). Comparative evaluation of several DNA binding dyes in the detection of apoptosis-associated chromatin degradation by flow cytometry. Cytometry 13, 137–143.
45. Teodoro, J. G. and Branton, P. E. (1997). Regulation of adoptosis by viral gene products. Journal of Virology 71, 1739–1746.
46. Thompson, C. B. (1995). Apoptosis in the pathogenesis and treatment of disease. Science 267, 1456–1462.
47. Van den Heuvel, S. J. L., Van Laar, T., Kast., W. M., Melief, C. J., Zantema, A., and Van der Eb, A.j. (1990). Association between the cellular p53 and the adenovirus 5 EIB-55kD proteins reduces the oncogenicity of Ad-transformed cells. EMBO Journal 9, 2621–2629.
48. Van Laar T., Steegenga wt et al. (1994). Bloom's Syndrome cells GM1492 lack detectable p53 protein but exhibit normal G1 cell-cycle arrest after UV irradiation. Oncogene. 9: 981–983
49. White, E. (1996). Life, death, and the pursuit of apoptosis. Genes and development 10, 1–15.
50. Wyllie, A. H. (1995). The genetic regulation of apoptosis. Current Opinion in Genetics and Development 5, 97–104.
51. Wyllie, A. H., Kerr, J. F. R., Currie, A. R. (1980). Cell death: The significance of apoptosis. International Review of Cytology 68, 251–306.
52. Zhuang, S.-M., Landegent, J. E., Verschueren, C. A. J., Falkenburg, J. H. F., Van Ormondt, H., Van der Eb, A. J., Noteborn, M. H. M. (1995). Apoptin, a protein encoded by chicken anemia virus, induces cell death in various human hematologic malignant cells in vitro. Leukemia 9 S1, 118–120.
53. Zhuang, S.-M., Shvarts, A., Van Ormondt, H., Jochemsen, A.-G. Van der Eb, A. J., Noteborn, M. H. M. (1995). Apoptin, a protein derived from chicken anemia virus, induces a p53-independent apoptosis in human osteosarcoma cells. Cancer Research 55, 486–489.

indicative of the transforming capability of said possible transforming agent, whereby the transforming capability of said possible transforming agent is determined as compared to non-transformed cells provided with apoptin apoptotic activity and a non-transforming agent.

2. The method according to claim 1 wherein said apoptotic activity is provided by transducing said cell with a recombinant nucleic acid molecule encoding apoptin.

3. The method according to claim 1, wherein said possible transforming agent is a proteinaceous substance, or a carcinogenic agent.

4. The method according to claim 3 wherein said proteinaceous substance is co-expressed in said non-transformed cell with said apoptotic activity.

5. The method according to claim 4, wherein said proteinaceous substance is the large T-antigen of SV40 capable of transforming said non-transformed cell.

6. A method for determining the predisposition of a cell to become a tumor cell, said method comprising:
providing said cell with inducible apoptin that has apoptotic activity,

What is claimed is:

1. A method for determining the transforming capability of a possible transforming agent, said method comprising:
providing a non-transformed cell with inducible apoptin apoptotic activity, exposing said cell to said possible transforming agent, and identifying either
(a) a shift in localization of said apoptotic activity to the nucleus of said cell, or
(b) induction of apoptosis in said cell, wherein identification of at least one of (a) or (b) in said cell is subjecting said cell to a mutagenic agent, and identifying either
(a) induction of apoptosis in said cell, or
(b) a shift in localization of said apoptotic activity to the nucleus of said cell, wherein identification of at least one of (a) or (b) is indicative of the predisposition of said cell to become a tumor cell, wherein said cell predisposed to become a tumor cell will have greater apoptotic activity compared to a normal cell upon exposure to said mutagenic agent, whereby the predisposition of said cell to become a tumor cell is determined.

7. A method for determining a gene mutation having at least one of oncogenic and transforming activity in a cell, said method comprising subjecting said cell to a method according to claim 6.

8. A method for determining the predisposition of a subject for hereditary types of cancer, said method comprising:
   providing a sample of cells of said subject with inducible apoptin that has apoptotic activity,
   subjecting said sample of cells to a mutagenic agent, and identifying either
   (a) induction of apoptosis in said sample of cells, or
   (b) a shift in localization of said apoptotic activity to the nucleus of a cell of said sample of cells, wherein identification of at least one of (a) or (b) is indicative of said subject comprising said sample of cells to hereditary types of cancer, wherein said sample of cells from a subject predisposed to hereditary types of cancer will have greater apoptotic activity compared to a sample of cells from a normal subject upon exposure to said mutagenic agent, whereby the predisposition for hereditary types of cancer of said subject comprising said sample of cells is determined.

9. The method according to claim 6 or 8 wherein said mutagenic agent is UV-irradiation or X-ray treatment.

10. A method for the detection of enhanced reactivation response in cells, said method comprising:
   providing said cells with inducible apoptin that has apoptotic activity,
   subjecting said cells to a mutagenic agent, and identifying either
   (a) induction of apoptosis in said cells, or
   (b) a shift in localization of said apoptotic activity to the nucleus of said cells, wherein identification of at least one of (a) or (b) in said cell is indicative of enhanced reactivation response in said cells, wherein said cells with enhanced reactivation response will have greater apoptotic activity compared to normal cells upon exposure to said mutagenic agent, whereby the cells with enhanced reactivation response in cells is determined.

* * * * *

UNITED STATES PATENT AND TRADEMARK OFFICE
CERTIFICATE OF CORRECTION

PATENT NO.    : 6,528,247 B1
DATED         : March 4, 2003
INVENTOR(S)   : Mathieu H. M. Noteborn It is certified that error appears in the above-identified patent and that said Letters Patent is hereby corrected as shown below:

<u>Title page,</u>
Item [57], ABSTRACT,
Line 2, change "and or" to -- and/or --
Line 5, change "related" to -- relates --
Item [56], OTHER PUBLICATIONS, 6th reference, change "Daneb" to -- Danen --; and 41$^{st}$ reference, change "Smiths" to -- Smits --

<u>Column 1,</u>
Line 20, change "stared" to -- stated --

<u>Column 3,</u>
Line 64, change "mid" to -- mild --

<u>Column 5,</u>
Line 35, change "1.0%" to -- 10% --

<u>Column 6,</u>
Line 56, change "monolayed" to -- monolayered --

<u>Column 7,</u>
Line 9, change "grove" to -- Grove --
Line 27, change "aoppotfic" to -- apoptotic --

<u>Column 9,</u>
Line 13, change "VH 10" to -- VH10 --

<u>Column 10,</u>
Line 5, delete the period after "a"
Line 20, change "proces" to -- process --

<u>Column 12,</u>
Line 24, change "pCKV-VP3" to -- pCMV-VP3 --
Line 37, change "(FO)" to -- (F0) --
Line 46, change "(NO:3)" to -- NO:3) --

UNITED STATES PATENT AND TRADEMARK OFFICE
CERTIFICATE OF CORRECTION

PATENT NO. : 6,528,247 B1
DATED : March 4, 2003
INVENTOR(S) : Mathieu H. M. Noteborn It is certified that error appears in the above-identified patent and that said Letters Patent is hereby corrected as shown below:

Column 13,
Line 37, change "apotosis" to -- apoptosis --

Column 14,
Line 7, change "8S.1" to -- 85.1 --
Line 43, change "M .H. M." to -- M. H. M. --

Column 15,
Line 16, change "12.2," to -- 122, --
Line 43, change "Wilms" to -- Wilms' --

Column 17,
Line 61, at the end of the line, after "apoptin" insert -- that has --

Signed and Sealed this

Sixteenth Day of September, 2003

JAMES E. ROGAN
*Director of the United States Patent and Trademark Office*